(12) United States Patent
Dochnahl et al.

(10) Patent No.: US 9,359,312 B2
(45) Date of Patent: Jun. 7, 2016

(54) PROCESS FOR MANUFACTURING BENZOXAZINONES

(71) Applicants: Maximilian Dochnahl, Mannheim (DE); Michael Rack, Eppelheim (DE); Michael Keil, Freinsheim (DE); Bernd Wolf, Niederkirchen (DE); Uwe Josef Vogelbacher, Ludwigshafen (DE); Joachim Gebhardt, Wachenheim (DE); Timo Frassetto, Mannheim (DE); Volker Maywald, Ludwigshafen (DE)

(72) Inventors: Maximilian Dochnahl, Mannheim (DE); Michael Rack, Eppelheim (DE); Michael Keil, Freinsheim (DE); Bernd Wolf, Niederkirchen (DE); Uwe Josef Vogelbacher, Ludwigshafen (DE); Joachim Gebhardt, Wachenheim (DE); Timo Frassetto, Mannheim (DE); Volker Maywald, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/365,829

(22) PCT Filed: Dec. 20, 2012

(86) PCT No.: PCT/EP2012/076373
§ 371 (c)(1),
(2) Date: Jun. 16, 2014

(87) PCT Pub. No.: WO2013/092856
PCT Pub. Date: Jun. 27, 2013

(65) Prior Publication Data
US 2014/0357861 A1    Dec. 4, 2014

(30) Foreign Application Priority Data
Dec. 23, 2011   (EP) .................................... 11195507

(51) Int. Cl.
*C07D 265/36*   (2006.01)
*C07D 413/04*   (2006.01)
*C07C 231/12*   (2006.01)

(52) U.S. Cl.
CPC ............ *C07D 265/36* (2013.01); *C07C 231/12* (2013.01); *C07D 413/04* (2013.01)

(58) Field of Classification Search
CPC ............................ C07D 265/34; C07C 231/12

USPC ........................................................ 544/105
See application file for complete search history.

(56) References Cited

FOREIGN PATENT DOCUMENTS

| EP | 0 237 899 | 9/1987 |
| WO | WO 2006/129100 | 12/2006 |
| WO | WO 2010/145992 | 12/2010 |

OTHER PUBLICATIONS

International Search Report, PCT/EP2012/076373, search completed Feb. 28, 2013.
International Preliminary Report on Patentability, PCT/EP2012/076373, report issued Jun. 24, 2014.
European Search Report, EP 11 19 5507, search completed May 25, 2012.
Cai et al., "Dication $C(R^1)$—$N(R^2)_2$ Synthons and their use in the Synthesis of Formamidines, Amidines, and alpha-Aminonitriles", Tetrahedron, vol. 56, No. 42, Oct. 13, 2000, pp. 8253-8262.
Johnson et al., "Nonenzymatic Conversion of Penicillins to 6-Aminopenicillanic Acid", The Journal of Organic Chemistry, vol. 31, No. 8, Aug. 1, 1966, pp. 2560-2564.
Reany et al., "A model system using modulation of lanthanide luminescence to signal Znin competitive aqueous media", Journal of The Chemical Society, Perkins Transactions 2, No. 9, Sep. 1, 2000, pp. 1819-1831.
Técher et al., "Amides tertiaires de l'acide oxo-3-dihydro-2,3 benzoxazine-1,4 carboxylique-2", Comptes Rendus Des Seances De L'Academie Des Sciences, Serie C:Sciences Chimiques, vol. 270, Jan. 1, 1970, pp. 107-110.
Office Action, issued in co-assigned U.S. Appl. No. 14/365,822, dated Jul. 29, 2015.

*Primary Examiner* — Kahsay Habte
(74) *Attorney, Agent, or Firm* — Brinks Gilson & Lione

(57) ABSTRACT

The present invention relates to a process for manufacturing a benzoxazinone of formula (I),

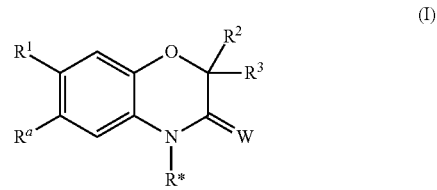

by reacting a nitro compound of formula (II) with a reducing agent to obtain an amino compound of formula (III), and then reacting the amino compound of formula (III) with an acid; wherein the variables are defined according to the description, and benzoxazinone of formula (I).

10 Claims, No Drawings

PROCESS FOR MANUFACTURING BENZOXAZINONES

This application is a National Stage application of International Application No. PCT/EP2012/076373, filed Dec. 20, 2012, the entire contents of which is hereby incorporated herein by reference. This application also claims priority under 35 U.S.C. §119 to EP Patent Application No. 11195507.6, filed Dec. 23, 2011,the entire contents of which is hereby incorporated herein by reference.

DESCRIPTION

The invention relates to benzoxazinones, a process for manufacturing these compounds, their use in and a process for manufacturing triazinon-benzoxazinones.

WO 2010/145992 discloses a process for the preparation of herbicidal benzoxazinones by reacting 2-amino-5-fluorophenol with sodium hydride followed by trapping with ethyl bromodifluoroacetate. Said process has, if scaled up, several disadvantages: The use of NaH on a large scale is dangerous due to the pyrophoric nature of the reagent. The base used during cyclization is DBU, which is rather expensive. Further, at a later stage, the reduction is made using stoichiometric amounts of both iron and ammonium chloride.

Hence, there is still room for improvement, specifically in view of economical and ecological aspects.

One task of the invention is to provide an efficient process for manufacturing benzoxazinones of formula (I).

It has been found that benzoxazinones of formula (I) can be obtained by reduction nitro compounds of formula (II) bearing a nitro group in the ortho-position of the aromatic ring, and subsequent acid-mediated cyclization of the intermediate.

A reductive cyclization of aryloxyacetic acid derivatives for preparing 2-unsubstituted benzoxazinones is disclosed in EP 0237899. However, the latter does not give any indication of a method for the synthesis of benzoxazinones of formula (I) according to the present invention.

It is therefore one object of the present invention to provide a process for manufacturing a benzoxazinone of formula (I),

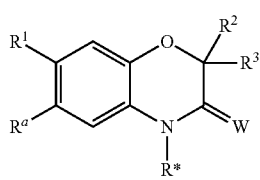
(I)

wherein
$R^1$ is H or halogen;
$R^2$ is halogen;
$R^3$ is H or halogen;
$R^a$ is H, halogen or $NH_2$;
$R^*$ is H or OH; and
W is O or S;
comprising
step (i): reacting a nitro compound of formula (II),

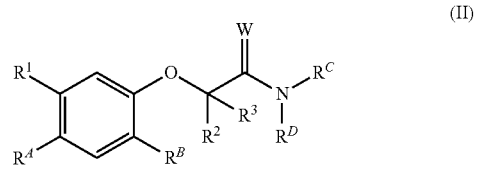
(II)

wherein $R^1$, $R^2$, $R^3$, W are defined as in formula (I);
$R^A$ is H, halogen, $NH_2$ or $NO_2$;
$R^B$ is $NO_2$; and
$R^C$, $R^D$ are independently of each other $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl or benzyl, wherein the phenyl and the benzyl ring are independently of one another unsubstituted or substituted with 1 to 5 substituents selected from the group consisting of halogen, $NO_2$, $C_1$-$C_6$-alkyl or $C_1$-$C_6$-alkoxy,
or $R^C$ and $R^D$ together with the N atom which they are attached to, represent a saturated or aromatic 3- to 6-membered ring, optionally containing 1 to 3 additional heteroatoms from the group O, S and N, with the ring optionally being substituted with 1 to 3 $C_1$-$C_6$-alkyl substituents;
with a reducing agent to obtain an amino compound of formula (III),

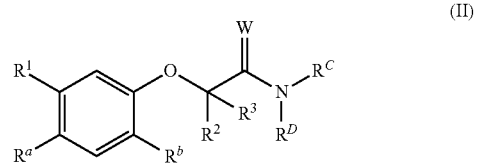
(II)

wherein $R^1$, $R^2$, $R^3$, $R^a$, W, $R^C$ and $R^D$ are defined as in formulae (I) or (II); and
$R^b$ is $NH_2$ or NHOH;
followed by
step (ii): reacting the amino compound of formula (III) with an acid.

In a further aspect of the invention there is provided a process for manufacturing triazinon-benzoxazinones of formula (IV),

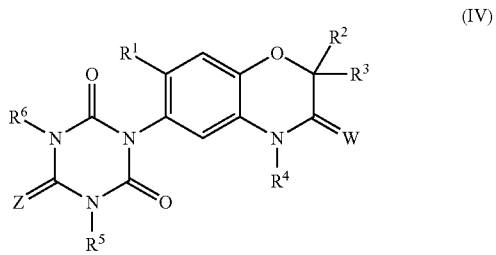
(IV)

wherein $R^1$, $R^2$, $R^3$ and W are defined as in formula (I);
$R^4$ is H, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;

$R^5$ is H, $NH_2$, $C_1$-$C_6$-alkyl or $C_3$-$C_6$-alkynyl;
$R^6$ is H or $C_1$-$C_6$-alkyl; and
Z is O or S.

In a further aspect of the invention there is provided the use of benzoxazinones of formula (I) in manufacturing triazinon-benzoxazinones of formula (IV).

In a further aspect of the invention there is provided the use of nitro compound of formula (II) in manufacturing triazinon-benzoxazinones of formula (IV).

In a further aspect of the invention there is provided the use of amino compounds of formula (III) in manufacturing triazinon-benzoxazinones of formula (IV).

The organic moieties mentioned in the definition of the variables according to the present invention, e.g. $R^1$ to $R^6$, $R^*$, $R^a$, $R^b$, $R^A$, $R^B$, $R^C$ and $R^D$ are—like the term halogen—collective terms for individual enumerations of the individual group members.

The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:

$C_1$-$C_4$-alkyl: for example $CH_3$, $C_2H_5$, n-propyl, $CH(CH_3)_2$ n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-cynaoalkyl, $C_1$-$C_6$-nitroalkyl, $C_1$-$C_6$-hydroxyalkyl, $C_1$-$C_6$-alkyoxy-$C_1$-$C_6$-alkyl, $C_3$-$C_6$-cycloalkyl-$C_1$-$C_4$-alkyl, amino-$C_1$-$C_6$-alkyl, ($C_1$-$C_6$-alkyl)amino-$C_1$-$C_6$-alkyl and di($C_1$-$C_6$-alkyl)amino-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, a $C_1$-$C_3$-haloalkyl radical as mentioned above, and also, for example, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl and also the cycloalkyl moieties of $C_3$-$C_6$-cycloalkyl-$C_1$-$C_6$-alkyl: monocyclic saturated hydrocarbons having 3 to 6 ring members, such as cyclopropyl, cyclobutyl, cyclopentyl and cyclohexyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkenyl: $C_3$-$C_6$-alkenyl as mentioned above, and also ethenyl;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_2$-$C_6$-alkynyl: $C_3$-$C_6$-alkynyl as mentioned above and also ethynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut- 2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

($C_1$-$C_4$-alkyl)amino: for example methylamino, ethylamino, propylamino, 1-methylethylamino, butylamino, 1-methylpropylamino, 2-methylpropylamino or 1,1-dimethylethylamino;

($C_1$-$C_6$-alkyl)amino and also the ($C_1$-$C_6$-alkyl)amino moieties of ($C_1$-$C_6$-alkyl)amino-$C_1$-$C_6$-alkyl: ($C_1$-$C_4$-alkylamino) as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino 3,3-dimethylbutylamino, 1-ethylbutylamino, 2-ethylbutylamino, 1,1,2-trimethylpropylamino, 1,2,2-trimethyl-propylamino, 1-ethyl-1-methylpropylamino or 1-ethyl-2-methylpropylamino;

di($C_1$-$C_4$-alkyl)amino: for example N,N-dimethylamino, N,N-diethylamino, N,N-di(1-methylethyl)amino, N,N-dipropylamino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$-$C_6$-alkyl)amino and also the di($C_1$-$C_6$-alkyl)amino moieties of di($C_1$-$C_6$-alkyl)amino-$C_1$-$C_6$-alkyl: di($C_1$-$C_4$-alkyl)amino as mentioned above, and also, for example, N-methyl-N-pentylamino, N-methyl-N-(1-methylbutyl)amino, N-methyl-N-(2-methylbutyl) amino, N-methyl-N-(3-methylbutyl)amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethylpropyl)amino, N-methyl-N-(1-methylpentyl)amino, N-methyl-N-(2-methylpentyl)amino, N-methyl-N-(3-methylpentyl)amino, N-methyl-N-(4-methylpentyl)amino, N-methyl-N-(1,1-dimethylbutyl) amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl) amino, N-methyl-N-(3,3-dimethylbutyl)amino, N-methyl-N-(1-ethylbutyl)amino, N-methyl-N-(2-ethylbutyl)amino, N-methyl-N-(1,1,2-trimethylpropyl) amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methylpentyl) amino, N-ethyl-N-(3-methylpentyl)amino, N-ethyl-N-(4-methylpentyl)amino, N-ethyl-N-(1,1-dimethylbutyl) amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl) amino, N-ethyl-N-(3,3-dimethylbutyl)amino, N-ethyl-N-(1-ethylbutyl)amino, N-ethyl-N-(2-ethylbutyl) amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

saturated or aromatic 3- to 6-membered ring optionally containing 1 to 3 additional heteroatoms selected from the group O, S and N:

a monocyclic, saturated or aromatic cycle having three to six ring members which comprises apart from one nitrogen atom and carbon atoms optionally additionally one to three heteroatoms selected from the group O, S and N, for example: 1-aziridinyl, 1-azetidinyl; 1-pyrrolidinyl, 2-isothiazolidinyl, 2-isothiazolidinyl, 1-pyrazolidinyl, 3-oxazolidinyl, 3-thiazolidinyl, 1-imidazolidinyl, 1,2,4-triazolidin-1-yl, 1,2,4-oxadiazolidin-2-yl, 1,2,4-oxadiazolidin-4-yl, 1,2,4-thiadiazolidin-2-yl, 1,2,4-thiadiazolidin-4-yl; 1-pyrrolyl, 1-pyrazolyl, 1-imidazolyl, 1,2,3-triazol-1-yl, 1,2,4-triazol-1-yl, 1-tetrazolyl; 1-piperidinyl, 1-hexahydropyridazinyl, 1-hexahydropyrimidinyl, 1-piperazinyl, 1,3,5-hexahydrotriazin-1-yl, 1,2,4-hexahydrotriazin-1-yl, tetrahydro-1,3-oxazin-1-yl, 1-morpholinyl;

The preferred embodiments of the invention mentioned herein below have to be understood as being preferred either independently from each other or in combination with one another.

According to a preferred embodiment of the invention preference is also given to the preparation of those benzoxazinones of formula (I), wherein the variables, either independently of one another or in combination with one another, have the following meanings:

$R^1$ is preferably H or F; particularly preferred H;
is also preferably halogen, particularly preferred F or Cl, especially preferred F;

$R^2$ is preferably Cl or F, particularly preferred F;

$R^3$ is preferably H, Cl or F, particularly preferred H or F, especially preferred H;

is also preferably halogen, particularly preferred F or Cl, especially preferred F;

$R^a$ is preferably H or halogen, particularly preferred H;

is also preferably halogen or $NH_2$, particularly preferred halogen;

is also preferred H or $NH_2$, particularly preferred $NH_2$;

$R^*$ is preferably H;

is also preferred OH;

W is preferably O, is also preferably S.

Particular preference is also given to the preparation of benzoxazinones of formula (Ia), which correspond to benzoxazinones of formula (I) wherein $R^3$ is F:

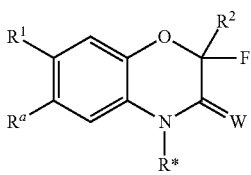
(Ia)

Particular preference is also given to the preparation of benzoxazinones of formula (Ia.1), which correspond to benzoxazinones of formula (I) wherein $R^3$ is F and $R^a$ is $NH_2$:

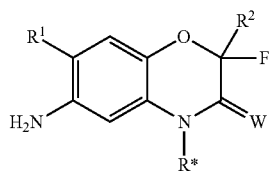
(Ia.1)

Particular preference is also given to the preparation of benzoxazinones of formula (Ia.2), which correspond to benzoxazinones of formula (I) wherein $R^2$ and $R^3$ are F and $R^a$ is $R^{aa}$ is halogen or $NH_2$:

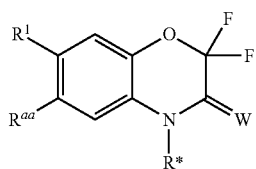
(Ia.2)

$R^{aa}$ in formula (Ia.2) is preferably halogen, also preferably $NH_2$.

Particular preference is also given to the preparation of benzoxazinones of formula (Ia.1.1), which correspond to benzoxazinones of formula (I) wherein $R^1$, $R^2$ and $R^3$ are F, $R^a$ is $NH_2$ and W is O:

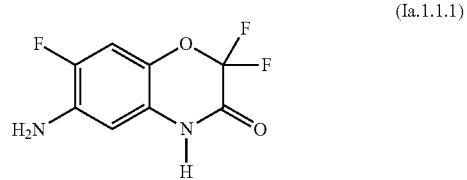 [SMILES: Nc1cc2c(cc1F)OC(F)(F)C(=O)N2]
(Ia.1.1)

Particular preference is also given to the preparation of the benzoxazinone of formula (Ia.1.1.1), which corresponds to benzoxazinones of formula (I) wherein $R^1$, $R^2$ and $R^3$ are F, $R^a$ is $NH_2$, $R^*$ is H and W is O:

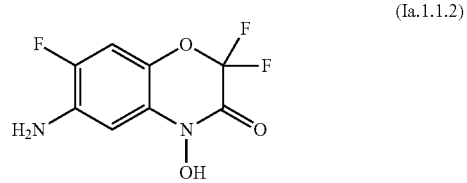 [SMILES: Nc1cc2c(cc1F)OC(F)(F)C(=O)N2O]
(Ia.1.1.1)

Particular preference is also given to the preparation of benzoxazinones of formula (Ia.1.1.2), which correspond to benzoxazinones of formula (I) wherein $R^1$, $R^2$ and $R^3$ are F, $R^a$ is $NH_2$, $R^*$ is OH and W is O:

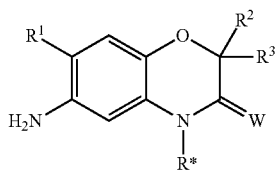
(Ia.1.1.2)

Particular preference is also given to the preparation of benzoxazinones of formula (Ib), which correspond to benzoxazinones of formula (I) wherein $R^a$ is $NH_2$:

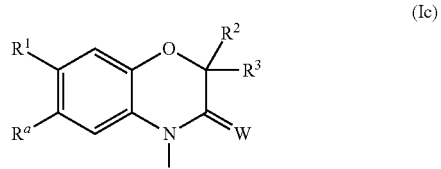
(Ib)

Particular preference is also given to the preparation of benzoxazinones of formula (Ic), which correspond to benzoxazinones of formula (I) wherein $R^*$ is OH:

(Ic)

With respect to the variables within the compounds of formulae (II) or (III), the particularly preferred embodiments of the compounds of formulae (II) or (III) correspond, either independently of one another or in combination with one another, to those of the variables of $R^1$, $R^2$, $R^3$, $R^a$, $R^*$ and W of formula (I), or have, either independently of one another or in combination with one another, the following meanings:

$R^b$ is preferably $NH_2$,
is also preferably NHOH;

$R^A$ is preferably halogen, $NH_2$ or $NO_2$,
particularly preferred $NH_2$ or $NO_2$,
especially preferred $NH_2$,
is also preferably halogen or $NH_2$,
particularly preferred halogen;
is also preferably halogen or $NO_2$,
particularly preferred $NO_2$;

$R^B$ is $NO_2$;

$R^C$ and $R^D$ preferably are independently of each other $C_1$-$C_6$-alkyl, $C_1$-$C_6$-cyanoalkyl, $C_1$-$C_6$-hydroxyalkyl, $C_1$-$C_6$-alkoxy-$C_1$-$C_6$-alkyl, $C_3$-$C_6$-cycloalkyl, phenyl or benzyl,
wherein the phenyl and the benzyl ring are independently of one another unsubstituted or substituted with 1 to 3 substituents selected from the group consisting of halogen, $C_1$-$C_6$-alkyl or $C_1$-$C_6$-alkoxy,
or $R^C$ and $R^D$ together with the N atom which they are attached to, represent a saturated or aromatic 5- to 6-membered ring, optionally containing 1 additional heteroatom from the group O and N, with the ring optionally being substituted with 1 to 2 $C_1$-$C_6$-alkyl substituents;

particularly preferred are independently of each other $C_1$-$C_4$-alkyl, $C_1$-$C_4$-hydroxyalkyl, $C_1$-$C_6$-alkoxy-$C_1$-$C_4$-alkyl or benzyl,
wherein the benzyl ring is unsubstituted or substituted by 1 to 3 substituents selected from the group consisting of halogen, $C_1$-$C_4$-alkyl or $C_1$-$C_4$-alkoxy,
especially preferred the benzyl ring is unsubstituted,
or $R^C$ and $R^D$ together with the N atom which they are attached to, represent a saturated 5- to 6-membered ring, optionally containing 1 additional oxygen atom, with the ring optionally being substituted with 1 to 2 $C_1$-$C_6$-alkyl substituents.

Particular preference is also given to the nitro compounds of formula (IIa) (corresponds to formula (II) wherein $R^1$, $R^2$ and $R^3$ are F, $R^A$ and $R^B$ are $NO_2$ and W is O),

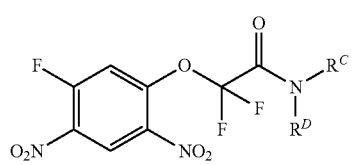

(IIa)

wherein the variables $R^C$ and $R^D$ have the meanings, in particular the preferred meanings, as defined above;

most preference to the nitro compounds of formulae (IIa.1) to (IIa.8) of Table A listed below, in which the variables $R^C$ and $R^D$ together have the meanings given in one row of Table A (compounds of formulae IIa.1 to IIa.8); and where the definitions of the variables $R^C$ and $R^D$ are of particular importance for the process and the compounds according to the invention not only in combination with one another but in each case also on their own:

TABLE A

| no. | $R^C$ | $R^D$ |
|---|---|---|
| IIa.1 | $CH_3$ | H |
| IIa.2 | $CH_3$ | $CH_3$ |
| IIa.3 | $CH_3$ | $CH(CH_3)_2$ |
| IIa.4 | $C_2H_5$ | $C_2H_5$ |
| IIa.5 | —$CH_2$—$CH_2$—$CH_2$—$CH_2$— | |
| IIa.6 | —$CH_2$—$CH_2$—$CH_2$—$CH_2$—$CH_2$— | |
| IIa.7 | —$CH_2$—$CH_2$—O—$CH_2$—$CH_2$— | |
| IIa.8 | —$CH_2$—$CH_2$—N($CH_3$)—$CH_2$—$CH_2$— | |

Particular preference is also given to the amino compounds of formula (IIIa) (corresponds to formula (III) wherein $R^1$, $R^2$ and $R^3$ are F, $R^a$ and $R^b$ are $NH_2$ and W is O),

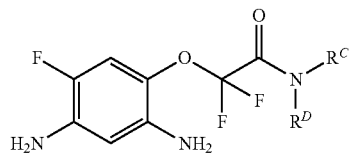

(IIIa)

wherein the variables $R^C$ and $R^D$ have the meanings, in particular the preferred meanings, as defined above;

most preference to the amino compounds of formulae (IIIa.1) to (IIIa.8) of Table B listed below, in which the variables $R^C$ and $R^D$ together have the meanings given in one row of Table B (compounds of formulae IIIa.1 to IIIa.8); and where the definitions of the variables $R^C$ and $R^D$ are of particular importance for the process and the compounds according to the invention not only in combination with one another but in each case also on their own:

TABLE B

| no. | $R^C$ | $R^D$ |
|---|---|---|
| IIIa.1 | $CH_3$ | H |
| IIIa.2 | $CH_3$ | $CH_3$ |
| IIIa.3 | $CH_3$ | $CH(CH_3)_2$ |
| IIIa.4 | $C_2H_5$ | $C_2H_5$ |
| IIIa.5 | —$CH_2$—$CH_2$—$CH_2$—$CH_2$— | |
| IIIa.6 | —$CH_2$—$CH_2$—$CH_2$—$CH_2$—$CH_2$— | |
| IIIa.7 | —$CH_2$—$CH_2$—O—$CH_2$—$CH_2$— | |
| IIIa.8 | —$CH_2$—$CH_2$—N($CH_3$)—$CH_2$—$CH_2$— | |

The process of the invention comprises two steps—a reduction [step (i)] and a cyclization [step (ii)].

In the first step [step (i)] the nitro compound of formula (II) is reacted with a reducing agent to obtain the amino compound of formula (III),

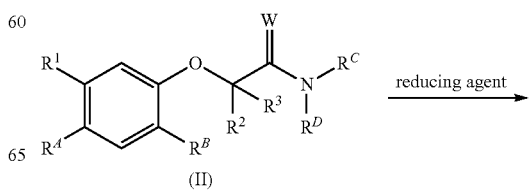

(II)

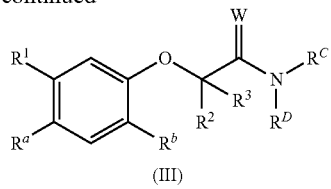

(III)

wherein the substituents are as herein defined.

Examples of suitable reducing agents and conditions are known from the literature and can be found inter alia in Advanced Organic Chemistry (ed. J. March), 4$^{th}$ edition, Wiley-Interscience, NY 1992, p. 1216 ff; or Organikum, 22$^{nd}$ edition, Wiley-VCH, Weinheim 2004, p. 626 ff.

Prominent examples are reducing agents like molecular hydrogen, hydrazine, formic acid, ammonium formate, borane or borohydrides in combination with a homogeneous or heterogeneous catalyst from metal salts of nickel, palladium, platinum, cobalt, rhodium, iridium, ruthenium or copper. Specific examples include palladium on charcoal, palladium on alumina, palladium on BaSO$_4$, platinum on charcoal, platinum on alumina, platinum(IV) oxide, Raney nickel, rhodium on alumina, ruthenium on alumina.

Further examples of suitable reducing agents are metals in their elemental form such as magnesium, iron, zinc, tin or metal salts such as tin(II) chloride in combination with an acid such as hydrochloric or acetic acid.

Further examples of suitable reducing agents are sulfur compounds like sodium hydrosulfite, rongalite, sodium sulfide, sodium hydrogen sulfide and ammonium polysulfide.

If the reducing agent contains an acid, the use of an additional acid is possible, but not necessary.

Even if the reducing agent does not contain an acid, the amino compound of formula (III) may at least partially cyclize to the benzoxazinone of formula (I) prior to adding the acid. However, if an acid is used, higher yields of the benzoxazinone of formula (I) can be obtained.

Preferred reducing agents include molecular hydrogen in combination with palladium on charcoal, palladium on alumina, palladium on BaSO$_4$, molecular hydrogen in combination with platinum on charcoal, platinum on alumina.

Especially preferred reducing agents are molecular hydrogen in combination with palladium on charcoal or platinum on charcoal.

A more preferred reducing agent is molecular hydrogen in combination with palladium on charcoal.

Also a more preferred reducing agent is molecular hydrogen in combination with platinum on charcoal.

The reduction allows for the use of molecular hydrogen in combination with a suitable catalyst, which facilitates the work-up of the reaction and reduces the amount of waste generated in the process.

The term reducing agent as used herein also includes mixtures of two or more, preferably two of the above compounds. Particular preference is given to the use of one reducing agent.

Accordingly, in a particularly preferred embodiment one reducing agent is employed in step (i).

The molar ratio of the nitro compound of formula (II) to the reducing agent is generally in the range of 1:2-15, preferably 1:2.5-10, more preferably 1:3-6.

The molar ratio of the nitro compound of formula (II) to the reducing agent is generally in the range of 1:2 to 1:15, preferably 1:2.5 to 1:10, more preferably 1:3 to 1:6.

Step (i) may be carried out under atmospheric pressure or under an elevated pressure of up to 20 bar, preferably up to 10 bar, more preferably up to 6 bar.

Step (i) is preferably carried out at an pH below 7, preferably at an pH in the range of 1 to 6; particularly preferred at an pH in the range of 1 to 5; especially preferred at an pH in the range of 2 to 4; more preferred at an pH in the range of 2 to 3.

The person skilled in the art may determine the pH by standard methods, for example by periodic or continuous measurement of the pH.

In one embodiment of the process according to the invention, the pH is determined before or at the beginning of step (i) and, if necessary adjusted accordingly by a respective amount of acid.

Suitable acids are inorganic acids like hydrochloric acid, hydrobromic acid, hydroiodic acid, phosphoric acid or sulfuric acid; mineral acids like hydrochloric acid, sulfuric acid, or phosphoric acid; as well as organic acids like formic acid, acetic acid, propionic acid, oxalic acid, methylbenzenesulfonic acid, benzenesulfonic acid, camphorsulfonic acid, citric acid.

Preferred acids are mineral acids and acetic acid as defined above.

Especially preferred is sulfuric acid.

In another embodiment of the process according to the invention, the nitro compounds of formula (II) necessary for the process according to the invention, are prepared and, after work-up, the resulting solution containing such nitro-compounds of formula (II) and having a pH below 7, preferably a pH in the ranges as mentioned above, is used in step (i). In such cases a further addition of acid might not be necessary. Such embodiment is preferred.

Preferably, step (i) is carried out in a solvent.

Examples of suitable solvents for the use in step (i) are water, alcohols such as methanol, ethanol, 1-propanol, 2-propanol, 1-butanol, 2-butanol, iso-butanol, tert-butanol, 2-ethyl-hexanol, hexafluoroisopropanol; aromatic hydrocarbons such as benzene, toluene, ethylbenzene, cymene, xylenes, mesitylene, benzotrifluoride; esters such as methyl acetate, ethyl acetate, n-butyl acetate, isobutyl acetate; ethers such as di-n-butyl ether, tert-butyl methyl ether (TBME), tetrahydrofuran (THF), 1,4-dioxane, 1,2-dimethoxyethane; aliphatic hydrocarbons such as hexanes, cyclohexane; dipolar aprotic solvents such as N,N-dimethylformamide (DMF), N,N-dibutylformamide, N,N-dimethylacetamide (DMAC), 1-methyl-2-pyrrolidinone (NMP), 1,3-dimethyl-2-imidazolidinone (DMI), N,N'-dimethylpropylene urea (DMPU), dimethyl sulfoxide (DMSO), sulfolane.

Preferred solvents include methanol, toluene and xylenes.

More preferred solvents include methanol and toluene.

The term solvent as used herein also includes mixtures of two or more of the above solvents. Preference is given to the use of methanol/toluene mixtures or methanol/xylenes mixtures. Particular preference is given to the use of methanol/toluene mixtures.

Step (i) is generally carried out at a temperature in the range of from 0° C. to the boiling point of the solvents, preferably in the range from 20 to 55° C., especially preferred in the range from 35 to 55° C., more preferably in the range from 35 to 45° C.

The nitro compound of formula (II) can be prepared as described further below.

In the second step [step (ii)] the amino compound of formula (III) is reacted with an acid to give the benzoxazinone of formula (I),

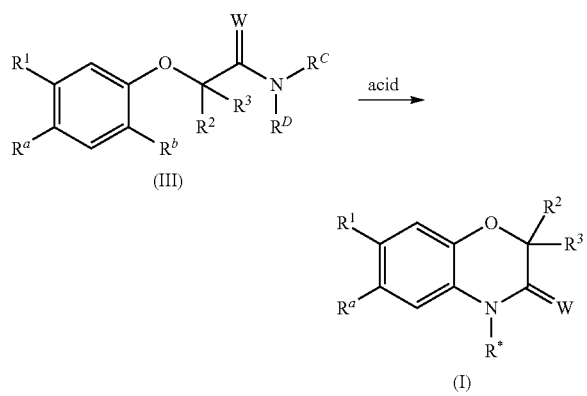

wherein the substituents are as herein defined.

Suitable acids are organic acids or inorganic acids.

Examples of suitable organic acids are formic acid, acetic acid, propionic acid, butyric acid, pivalic acid, succinic acid, adipic acid, maleic acid, fumaric acid, citric acid, chloroacetic acid, dichloroacetic acid, trichloroacetic acid, bromoacetic acid, trifluoroacetic acid, benzoic acid, nitrobenzoic acid, methanesulfonic acid, trifluoromethanesulfonic acid (triflic acid), bis(trifluoromethane)sulfonimide (triflimide), camphorsulfonic acid, benzenesulfonic acid, para-toluenesulfonic acid, nitrobenzenesulfonic acid or dinitrobenzenesulfonic acid.

Examples of suitable inorganic acids are hydrochloric acid, hydrobromic acid, hydroiodic acid, hydrofluoric acid, sulfuric acid, nitric acid, phosphoric acid, boric acid, tetrafluoroboric acid, hexafluorophosphoric acid or hexafluorosilicic acid.

Preferred acids include acetic acid, hydrochloric acid, hydrobromic acid, phosphoric acid, sulfuric acid and nitric acid.

More preferred acids include hydrochloric acid, sulfuric acid and acetic acid. Especially preferred acids are hydrochloric acid and sulfuric acid.

The term acid as used herein also includes mixtures of two or more, preferably two of the above compounds. Particular preference is given to the use of one acid.

Accordingly, in a particularly preferred embodiment one acid is employed in step (ii).

The cyclization does not require a rather expensive reagent such as DBU, but allows for the use of an acid like hydrochloric acid which is fairly inexpensive. Moreover, the process of the invention can be carried in one pot leading to higher yields, shorter batch times, lower cost of goods, and a reduced amount of waste.

The molar ratio of the nitro compound of formula (II) to the acid is generally in the range of 1:0.5-10, preferably 1:1-2, more preferably 1:1.

The molar ratio of the nitro compound of formula (II) to the acid is generally in the range of 1:0.5 to 1:10, preferably 1:1 to 1:2, more preferably 1:1.

Preferably, step (ii) is carried out in a solvent.

Suitable solvents for the use in step (ii) are, for example, the ones that are suitable for the use in step (i).

Preferred solvents include methanol, ethanol, isopropanol, toluene, xylenes and water. More preferred solvents include methanol, toluene and water.

The term solvent as used herein also includes mixtures of two or more of the above compounds.

Particular preference is given to the use of methanol/toluene/water mixtures.

In a particular embodiment, the solvent is not exchanged between carrying out steps (i) and (ii).

Step (ii) is generally carried out at a temperature in the range of from 0° C. to the boiling point of the solvent, preferably in the range of from 25 to 80° C., more preferably in the range of from 50 to 65° C.

In one embodiment the amino compound of formula (III) is isolated prior to being used in step (ii).

In another embodiment the amino compound of formula (III) is not isolated, and the reaction mixture obtained in step (i) is directly used in step (ii).

In a preferred embodiment with the reducing agent being molecular hydrogen in combination with a catalyst, a mixture of compound (II), the catalyst, and a solvent are stirred at a temperature in the range of from 20 to 60° C., preferably 40 to 45° C., for 2 to 8 h, preferably 3 to 4 h, in the presence of hydrogen at a pressure in the range of from 0 to 20 bar, preferably 0 to 5 bar. After completion or partial completion of step (i), the hydrogen source is removed. The catalyst is optionally filtered off. The acid is subsequently added, and the reaction mixture is stirred at a temperature in the range of from 20 to 65° C., preferably 50 to 65° C., for 0.5 to 5 h, preferably 0.5 to 2 h.

After completion or partial completion of the cyclization reaction, the respective mixture can be worked up by means of standard techniques. Examples thereof include extraction, filtration, aqueous work-up, distilling off solvents and/or other volatile compounds. These methods can also be combined with each other.

In a preferred embodiment the reaction mixture is brought to room temperature and the catalyst is filtered off. The pH of the filtrate is adjusted to slightly basic, preferably 7 to 10, more preferably 9, and the solvent is partly or completely distilled off. The product precipitates upon cooling, preferably to a temperature in the range of from 0 to 30° C. and/or adding water. The precipitated product can be isolated by filtration.

In a preferred embodiment the catalyst is filtered off from the reaction mixture in a temperature range of 50 to 60° C. The filter cake is washed with methanol up to three times. The pH of the filtrate is adjusted to slightly basic, preferably 7 to 10, more preferably 9. After addition of water the product precipitates in a temperature range from 0 to 30° C. The precipitated product can be isolated by filtration.

In a preferred embodiment the catalyst is filtered off from the reaction mixture and the filtrate is brought to room temperature. The pH of the filtrate is adjusted to slightly basic, preferably 7 to 10, more preferably 9. After addition of water the product precipitates in a temperature range from 0 to 30° C. The precipitated product can be isolated by filtration.

The product can be used without further purification or it can be purified using standard techniques, for example precipitation, recrystallization or column chromatography.

In a preferred embodiment, the product is isolated by precipitation.

In a further aspect of the invention there are provided benzoxazinones of formula (Ia.2), which correspond to benzoxazinones of formula (I) wherein $R^2$ and $R^3$ are F and $R^a$ is $R^{aa}$ is halogen or $NH_2$:

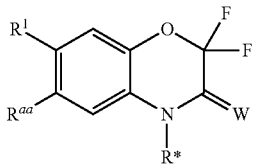

(Ia.2)

wherein $R^1$ is H or halogen;

$R^{aa}$ is halogen or $NH_2$; preferably halogen; also preferably $NH_2$;

$R^*$ is H or OH; and

W is O or S.

With respect to the variables within the compounds of formula (Ia.2), the particularly preferred embodiments of the compounds of formula (Ia.2) correspond, either independently of one another or in combination with one another, to those of the variables $R^1$, $R^*$ and W of formula (I).

In another aspect of the invention there are provided benzoxazinones of formula (Ia.1.1), which correspond to benzoxazinones of formula (I) wherein $R^1$, $R^2$ and $R^3$ are F, $R^a$ is $NH_2$ and W is O:

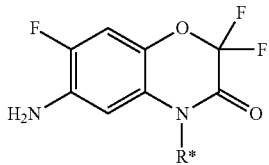

(Ia.1.1)

wherein $R^*$ is H or OH.

With respect to the variables within the compounds of formula (Ia.1.1), the particularly preferred embodiments of the compounds of formula (Ia.1.1) correspond, either independently of one another or in combination with one another, to those of the variable $R^*$ of formula (I).

In another aspect of the invention there is provided the benzoxazinone of formula (Ia.1.1.1), which corresponds to the benzoxazinone of formula (I) wherein $R^1$, $R^2$ and $R^3$ are F, $R^a$ is $NH_2$, $R^*$ is H and W is O:

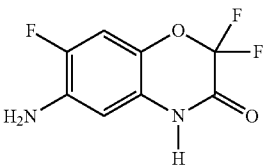

(Ia.1.1.1)

In another aspect of the invention there are provided benzoxazinones of formula (Ic), which correspond to benzoxazinones of formula (I) wherein $R^*$ is OH:

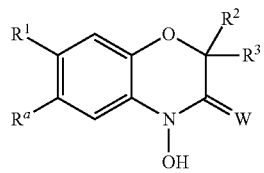

(Ic)

wherein $R^1$ is H or halogen;

$R^2$ is halogen;

$R^3$ is H or halogen;

$R^a$ is H, halogen or $NH_2$; and

W is O or S.

With respect to the variables within the compounds of formula (Ic), the particularly preferred embodiments of the compounds of formula (Ic) correspond, either independently of one another or in combination with one another, to those of the variables $R^1$, $R^2$, $R^3$, $R^a$ and W of formula (I).

NH-benzoxazinones of formula (I-1) (corresponding to benzoxazinones of formula (I) wherein $R^a$ is $NH_2$ and $R^*$ is H) are useful in the synthesis of 4-substituted amino-benzoxazinones of formula (V-1):

4-substituted amino-benzoxazinones of formula (V-1) can be prepared by reacting NH-benzoxazinones of formula (I-1) with a base and a compound of formula (VI), $R^\#L^\#$:

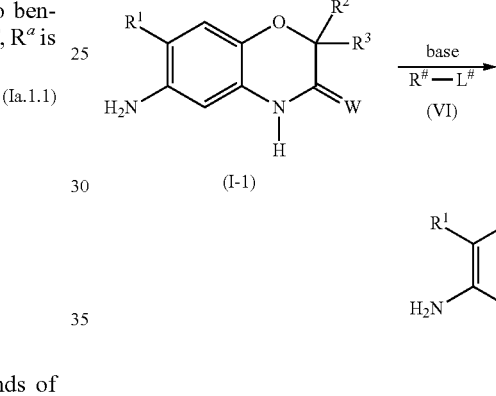

wherein $R^\#$ is $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;

$L^\#$ is halogen or $OS(O)_2R^7$;

$R^7$ is $C_1$-$C_6$-alkyl, $C_1$-$C_6$-haloalkyl, $C_1$-$C_6$-nitroalkyl, $C_1$-$C_6$-alkoxy-$C_1$-$C_6$-alkyl, $C_3$-$C_6$-cycloalkyl, phenyl or phenyl-$C_1$-$C_6$-alkyl, wherein each phenyl ring independently of one another is unsubstituted or substituted by 1 to 5 substituents selected from the group consisting of halogen, CN, $NO_2$, $C_1$-$C_6$-alkyl, $C_1$-$C_6$-haloalkyl or $C_1$-$C_6$-alkoxy; and $R^1$, $R^2$, $R^3$ and W are defined as in formula (I) above.

The NH-benzoxazinone of formula (I-1) that is converted into the 4-substituted amino-benzoxazinone of formula (V-1) can also be used in the form of a salt, for example in form of its alkali metal or alkaline metal salt, preferably in the form of its lithium, sodium or potassium salt. If a salt of the NH-benzoxazinone of formula (I-1) is used, the addition of a base is not necessary.

The compounds of formula (VI), $R^\#$-$L^\#$, necessary for the preparation of the 4-substituted amino-benzoxazinone of formula (V-1), are commercially available, or can be prepared by methods known in the art, e.g. Houben-Weyl 1985, EII-2, p. 1084.

Accordingly, in a further preferred embodiment of the process of the invention 4-substituted-amino-benzoxazinones of formula (V-1) are prepared by
i) reacting dinitro compounds of formula (II-1),

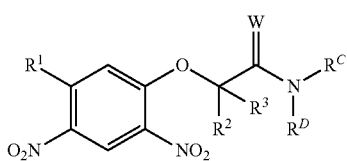

(II-1)

wherein $R^1$, $R^2$, $R^3$, $R^C$, $R^D$ and W are defined as in formula (II) above;
with a reducing agent to obtain diamino compounds of formula (III-1),

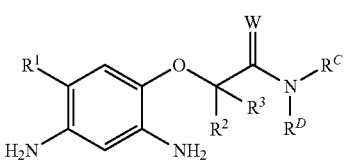

(III-1)

wherein $R^1$, $R^2$, $R^3$, $R^C$, $R^D$ and W are defined as in formula (III) above;
ii) treating the diamino compound of formula (III-1) with an acid to obtain NH-benzoxazinones of formula (I-1); and
iii) reacting the NH-benzoxazinone of formula (I-1) with a base and a compound of formula (VI) to obtain the 4-substituted amino-benzoxazinone of formula (V-1).

The term "amino-benzoxazinones of formula (VII)" combines NH-benzoxazinones of formula (I-1) and 4-substituted amino-benzoxazinones of formula (V-1):

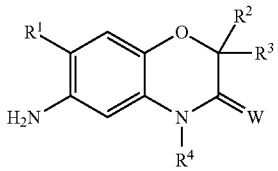

(VII)

wherein
$R^4$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl; and
$R^1$, $R^2$, $R^3$ and W are defined as in formula (I) above.

Accordingly, NH-benzoxazinones of formula (I-1) correspond to amino-benzoxazinones of formula (VII), wherein $R^4$ is hydrogen.

Accordingly, 4-substituted amino-benzoxazinones of formula (V-1) correspond to amino-benzoxazinones of formula (VII), wherein $R^4$ is $R^\#$, which is $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl.

Amino-benzoxazinones of formula (VII) are useful in the synthesis of triazinon-benzoxazinones of formula (IV):

Triazinon-benzoxazinones of formula (IV) can be prepared by reacting amino-benzoxazinones of formula (VII), wherein $R^4$ is H or $R^\#$ as defined in formula (VI), with 1,1'-carbonyldiimidazole (CDI) and a (thio)urea compound of formula (VIII):

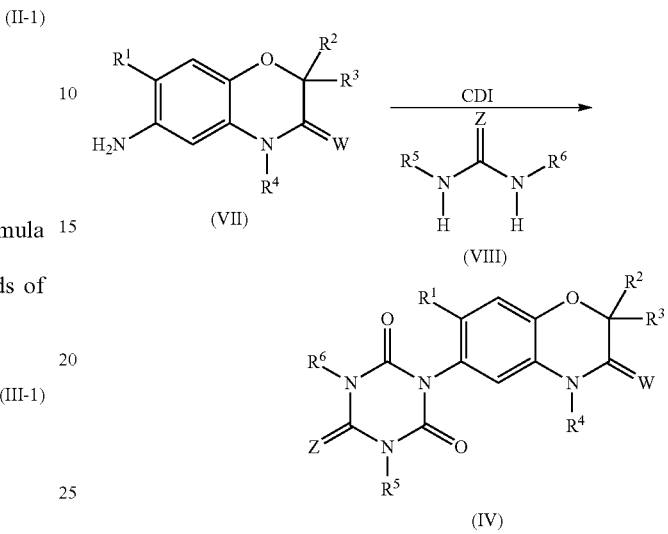

(VII)

(VIII)

(IV)

wherein
$R^1$, $R^2$, $R^3$, $R^4$, $R^5$, $R^6$, W and Z are defined as in formula (IV) above.

Preferably, the reaction of the amino-benzoxazinone of formula (VII) with 1,1'-carbonyldiimidazole (CDI) and the (thio)urea compound of formula (VIII) to obtain the triazinon-benzoxazinone of formula (IV) is carried out in the presence of a base.

Accordingly, in a further preferred embodiment of the process of the invention triazinon-benzoxazinones of formula (IV) are obtained by
i) reacting a dinitro compound of formula (II-1) with a reducing agent to obtain a diamino compound of formula (III-1);
ii) treating the diamino compound of formula (III-1) with an acid to obtain an amino-benzoxazinone of formula (I-1);
iii) optionally, reacting the NH-benzoxazinone of formula (I-1) with a base and a compound of formula (VI) to obtain the 4-substituted amino-benzoxazinone of formula (V-1); and
iv) reacting the amino-benzoxazinone of formula (VII), wherein $R^4$ is H or $R^\#$, with 1,1'-carbonyldiimidazole (CDI) and a (thio)urea compound of formula (VIII).

In another embodiment of the process according to the invention, the NH-benzoxazinone of formula (I-1) is further converted into a triazinon-benzoxazinone of formula (IV),

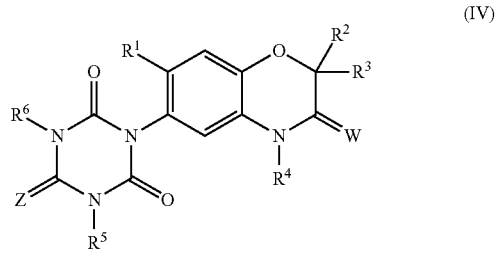

(IV)

wherein
R¹ is H or halogen;
R² is halogen;
R³ is H or halogen;
R⁴ is H, $C_1$-$C_6$ alkyl, $C_1$-$C_6$ haloalkyl, $C_3$-$C_6$ cycloalkyl, $C_3$-$C_6$ alkenyl, $C_3$-$C_6$ haloalkenyl, $C_3$-$C_6$ alkynyl, $C_3$-$C_6$ haloalkynyl, $C_1$-$C_6$ alkoxy or $C_3$-$C_6$-cycloalkyl-$C_1$-$C_6$-alkyl;
R⁵ is H, $NH_2$, $C_1$-$C_6$ alkyl or $C_3$-$C_6$ alkynyl;
R⁶ is H or $C_1$-$C_6$ alkyl;
W is O or S; and
Z is O or S;
by
iii) optionally reacting the NH-benzoxazinone of formula (I-1) with a base and a compound of formula (VI), $$R^\#\text{-}L^\# \quad (VI)$$

wherein
R# is $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
L# is halogen or $OS(O)_2R^7$; and
R⁷ is $C_1$-$C_6$-alkyl, $C_1$-$C_6$-haloalkyl, $C_1$-$C_6$-nitroalkyl, $C_1$-$C_6$-alkoxy-$C_1$-$C_6$-alkyl, $C_3$-$C_6$-cycloalkyl, phenyl or phenyl-$C_1$-$C_6$-alkyl, wherein each phenyl ring independently of one another is unsubstituted or substituted by 1 to 5 substituents selected from the group consisting of halogen, CN, $NO_2$, $C_1$-$C_6$-alkyl, $C_1$-$C_6$-haloalkyl or $C_1$-$C_6$-alkoxy;
to obtain a 4-substituted amino-benzoxazinone of formula (V-1),

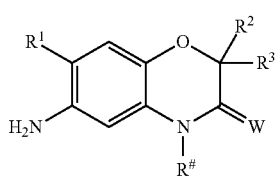
(V-1)

wherein R¹, R², R³ and W are defined as in formula (IV); and
R# is defined as in formula (VI); and
iv) reacting the amino-benzoxazinone of formula (VII),

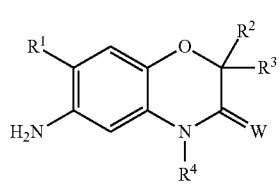
(VII)

wherein R¹, R², R³ and W are defined as in formula (IV); and
R⁴ is H or R# as defined in formula (VI);
with 1,1'-carbonyldiimidazole (CDI) and a (thio)urea compound of formula (VIII),

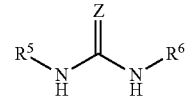
(VIII)

wherein R⁵, R⁶ and Z are defined as in formula (IV);
to obtain the triazinon-benzoxazinone of formula (IV).

In a preferred embodiment step iv) is carried out in the presence of a base.

The nitro compounds of formula (II) can be obtained by reacting haloacetamides of formula (IX) with phenols of formula (X-1) in the presence of a base:

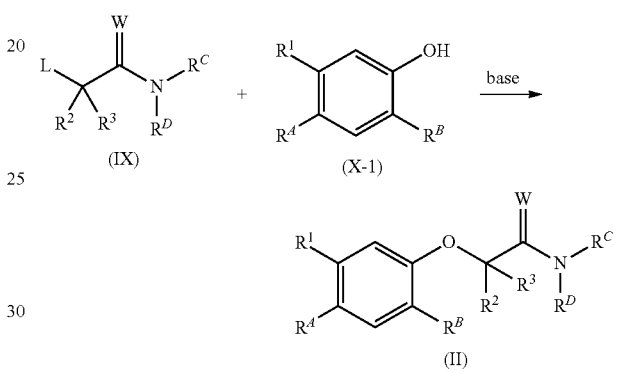

wherein
L is halogen; and
R¹, R², R³, R⁴, R$^B$ R$^C$, R$^D$ and W are defined as in formula (II) above.

The phenol of formula (X-1) that is converted into the nitro compound of formula (II) can also be used in the form of a salt, for example in form of its alkali metal or alkaline metal salt, preferably in the form of its sodium, potassium, magnesium or calcium salt. If a salt of the phenol of formula (X-1) is used, the addition of a base is not necessary.

In a preferred embodiment of the invention the nitro compounds of formula (II) are dinitro compounds of formula (II-1), which correspond to nitro compounds of formula (II) wherein R⁴ is $NO_2$.

The dinitro compounds of formula (II-1) can be prepared by reacting haloacetamides of formula (IX) with phenols of formula (X-2) in the presence of a base to give aryloxyacetamides of formula (XI) and, if R⁴ in formula (XI) is H, subsequently treating the aryloxyacetamides of formula (XI) with $HNO_3/H_2SO_4$:

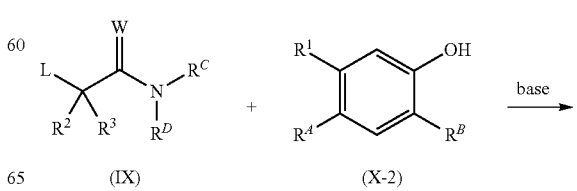

-continued

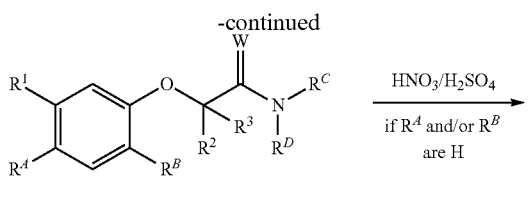

wherein
$R^A$ is H or $NO_2$;
L is halogen; and
$R^1, R^2, R^3, R^B, R^C, R^D$ and W are defined as in formula (II) above.

The phenol of formula (X-2) that is converted into the aryloxyacetamide of formula (XI) can also be used in the form of a salt, for example in form of its alkali metal or alkaline metal salt, preferably in the form of its sodium, potassium, magnesium or calcium salt. If a salt of the phenol of formula (X-2) is used, the addition of a base is not necessary.

Accordingly, in a further preferred embodiment of the process of the invention dinitro compounds of formula (II-1) are prepared by a) reacting haloacetamides of formula (IX) with a phenol of formula (X-2) in the presence of a base to obtain aryloxyacetamides of formula (XI); and,
b) if $R^A$ and/or $R^B$ in formula (XI) are H, reacting the aryloxyacetamides of formula (XI) with $HNO_3/H_2SO_4$.

With respect to the variables within the compounds of formulae (I-1), (II-1), (III-1), (IV), (V-1), (VI), (VII), (VIII), (IX), (X-1), (X-2) or (XI), the particularly preferred embodiments of the compounds of formulae (I-1), (II-1), (III-1), (IV), (V-1), (VI), (VII), (VIII), (IX), (X-1), (X-2) or (XI) correspond, either independently of one another or in combination with one another, to those of the variables of $R^1$, $R^2$, $R^3$, $R^C$, $R^D$ and W of formulae (I), (II) or (III), or have, either independently of one another or in combination with one another, the following meanings:

L is preferably Cl, Br or I, particularly preferred Cl or Br, especially preferred Br;
$R^4$ is preferably $C_3$-$C_6$-alkynyl or $C_3$-$C_6$-haloalkynyl, more preferably $C_3$-alkynyl or $C_3$-haloalkynyl, particularly preferred $CH_2C\equiv CH$, $CH_2C\equiv CCl$ or $CH_2C\equiv CBr$;
is also preferably $C_3$-$C_6$-alkynyl or $C_3$-$C_6$-cycloalkyl-$C_1$-$C_6$-alkyl, particularly preferred propargyl or cyclopropylmethyl;
is also preferably $C_3$-$C_6$-alkynyl, more preferably $C_3$-alkynyl; particularly preferred $CH_2C\equiv CH$;
is also preferably $C_3$-$C_6$-haloalkynyl, more preferably $C_3$-haloalkynyl, particularly preferred $CH_2C\equiv CCl$ or $CH_2C\equiv CBr$;
$R^5$ is preferably $NH_2$, $C_1$-$C_6$-alkyl or $C_3$-$C_6$-alkynyl; also preferably H or $C_1$-$C_6$-alkyl; more preferably $C_1$-$C_6$-alkyl; most preferably $C_1$-$C_4$-alkyl; particularly preferred $CH_3$;
$R^6$ is preferably $C_1$-$C_6$-alkyl; more preferably $C_1$-$C_4$-alkyl; most preferably $CH_3$;

Z is preferably O,
is also preferably S;
$R^\#$ is preferably $C_3$-$C_6$-alkynyl or $C_3$-$C_6$-haloalkynyl, more preferably $C_3$-alkynyl or $C_3$-haloalkynyl, particularly preferred $CH_2C\equiv CH$, $CH_2C\equiv CCl$ or $CH_2C\equiv CBr$;
is also preferably $C_3$-$C_6$-alkynyl or $C_3$-$C_6$-cycloalkyl-$C_1$-$C_6$-alkyl, particularly preferred propargyl or cyclopropylmethyl;
is also preferably $C_3$-$C_6$-alkynyl, more preferably $C_3$-alkynyl; particularly preferred $CH_2C\equiv CH$;
is also preferably $C_3$-$C_6$-haloalkynyl, more preferably $C_3$-haloalkynyl, particularly preferred $CH_2C\equiv CCl$ or $CH_2C\equiv CBr$;
$L^\#$ is preferably halogen or $OS(O_2)R^7$,
wherein $R^7$ is $C_1$-$C_6$-alkyl, phenyl or phenyl-$C_1$-$C_6$-alkyl, wherein each phenyl ring independently of one another is unsubstituted or substituted by 1 to 3 $C_1$-$C_6$-alkyl substituents;
particularly preferred halogen or $OS(O_2)R^7$,
wherein $R^7$ is $C_1$-$C_6$-alkyl or phenyl, wherein the phenyl ring is unsubstituted or substituted by 1 to 3 $C_1$-$C_6$-alkyl substituents;
especially preferred Cl, Br, $OS(O)_2CH_3$ or $OS(O)_2(C_6H_4)CH_3$.

The invention is illustrated by the following examples without being limited thereto or thereby.

1. Preparation of Benzoxazinones of Formula (I)

EXAMPLE 1.1

Synthesis of 6-amino-2,2,7-trifluoro-4H-benzo-[1,4]-oxazin-3-one from 2,2-difluoro-2(2,4-dinitro-5-fluoro-phenoxy)]-N,N-dimethyl-acetamide

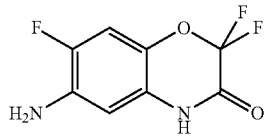

To a solution of 2,2-difluoro-2-(2,4-dinitro-5-fluoro-phenoxy)-N,N-dimethyl-acetamide (60.0 g, 186 mmol) in toluene (432 g) was added Pd on charcoal (5% Pd, 50% water content, 1.1 mmol). Thereafter MeOH (492 g) was added and the mixture was stirred under an atmosphere of hydrogen (over pressure 0.1 bar) at 45° C. for 2 h. After completion of the reaction the pressure was released, concentrated HCl (36.5%, 22 g, 220 mmol) added and the reaction mixture heated to reflux for further 1 h. The catalyst was filtered off, the pH adjusted with NaOH to 9 and the MeOH distilled off under reduced pressure. After addition of water (200 g) and stirring for 1 h the precipitate was filtered off, washed twice with water (100 g) and dried at 50° C. under reduced pressure. The product was obtained as a tan solid (38.9 g, 90% pure by NMR, 160 mmol, 86% yield).

$^1$H NMR (DMSO-$d_6$, 500 MHz): δ (ppm)=11.9 (bs, 1 H); 7.15 (d, J=11.0 Hz, 1 H); 6.55 (d, J=8.5 Hz, 1 H); 5.28 (bs, 2 H).

$^{13}$C NMR (DMSO-d$_6$, 125 MHz): δ (ppm)=153.7 (t, J=38 Hz); 146.1 (d, J=235 Hz); 133.9 (d, J=15 Hz); 127.3 (d, J=11 Hz); 120.9 (d, J=3 Hz); 113.1 (t, J=260 Hz); 104.9 (d, J=24 Hz); 102.4 (d, J=5 Hz).

EXAMPLE 1.2

Synthesis of 6-amino-2,2,7-trifluoro-4-hydroxy-4H-benzo-[1,4]-oxazin-3-one from 2,2-difluoro-2-(2,4-dinitro-5-fluoro-phenoxy)]-N,-dimethyl-acetamide

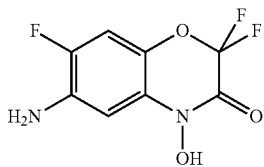 [SMILES: Nc1cc2c(cc1F)OC(F)(F)C(=O)N2O]

To a solution of 2,2-difluoro-2-(2,4-dinitro-5-fluoro-phenoxy)-N,N-dimethyl-acetamide (22.6 g, 70 mmol) in toluene (57 g) was added Pd on charcoal (5% Pd, 50% water content, 1.3 mmol). Thereafter MeOH (79 g) and sulphuric acid (20.5 g) were added and the mixture was stirred under an atmosphere of hydrogen (over pressure 0.1 bar) at 25° C. for 3 h. After completion of the reaction the pressure was released and the catalyst was filtered off. The filtrate was evaporated to dryness. The residue was dissolved in water (300 g), the pH adjusted with NaOH to 6.2 at 10° C. and three times extracted with ethyl acetate. After drying over MgSO$_4$ the ethyl acetate was distilled off under reduced pressure. The product was obtained as a tan solid (15.3 g, 50% pure by NMR, 33 mmol, 49% yield). The product can be purified by column chromatography. $^1$H NMR (DMSO-d$_6$, 500 MHz): δ (ppm)=11.75 (bs, 1 H); 7.20 (d, 1 H); 6.85 (d, 1 H); 6.10 (s, 2 H).

$^{13}$C NMR (DMSO-d$_6$, 125 MHz): δ (ppm)=149.6 (s); 146.0 (s); 134.1 (s); 124.9 (s); 123.2 (s); 114.5 (s); 104.8 (d); 100.2 (d).

2. Preparation of Nitro Compounds of Formula (II)

EXAMPLE 2.1

Synthesis of 2,2-difluoro-2-(2,4-dinitro-5-fluoro-phenoxy)-N,N-dimethyl-acetamide

Alternative 1:
To a mixture of H$_2$SO$_4$ (98%, 34.5 g, 345 mmol) and HNO$_3$ (100%, 11.0 g, 175 mmol) at room temperature was added 2,2-difluoro-2-(3-fluoro-phenoxy)-N,N-dimethyl-acetamide (8.7 g, 37 mmol). The temperature rose to 40° C. and was kept at that temperature for further 3 h. The mixture was then poured on 100 g of ice-water. The precipitate was taken up in 50 g of toluene and the aqueous phase was extracted with 25 g of toluene. The combined org. phases were washed with saturated NaHCO$_3$ solution and water. The crude product (11.5 g, 82% purity by quant. HPLC, 29 mmol, 78% yield) was obtained after removal of all volatiles as a yellowish solid. Analytically pure material the crude material could be obtained after recrystallisation from cyclohexane/EtOAc (80:20).

Alternative 2:
A solution of 61.5 g HNO$_3$ (100%, 0.976 mol) and 433.7 g H$_2$SO$_4$ (96%, 4.245 mol) was prepared at 0-20° C. by addition of HNO$_3$ to the sulfuric acid (quantity of mixed acid: 495.2 g). 100 g 2,2-difluoro-2-(3-fluoro-phenoxy)-N,N-dimethyl-acetamide (99%, 0,425 mol) was filled into the reaction vessel at 0° C. 236.9 g of the mixed acid (portion 1) was added at a rate to keep the temperature between 0 and 10° C.

258.3 of the mixed acid (portion 2) was dosed at 40° C. Upon complete addition the mixture was kept at 40° C. for another 9 h. Then, it was cooled to 25° C. and poured to a mixture of 1000 g ice water and 500 ml toluene. Reactor was rinsed with 100 g water and 50 g toluene. The phases were separated at 20° C. The aqueous layer was extracted with 240 g toluene and then discarded. The combined organic layers were washed 4 times with 400 g water in each case (final pH-value of the organic phase: 3). The water in the remaining organic phase was removed by distilling off toluene/water at reduced pressure. The product was obtained as a solution in toluene: 541.3 g (concentration of the nitro compound by quant. HPLC: 22.3%; yield: 88.1%).

$^1$H NMR (CDCl$_3$, 400 MHz): δ (ppm)=8.82 (d, J=7.5 Hz, 1 H); 7.52 (d, J=11.0 Hz, 1 H); 3.26 (s, 3 H); 3.11 (s, 3 H).

$^{13}$C NMR (CDCl$_3$, 100 MHz): δ (ppm)=157.1 (d, J=276 Hz); 156.7 (d, J=34 Hz); 147.6 (td, J=3 Hz, J=11 Hz); 136.9; 132.9 (d, J=9 Hz); 124.2; 115.3 (t, J=281 Hz); 111.7 (td, J=3 Hz, J=26 Hz); 36.8; 36.7.

Melting point: 66° C.

EXAMPLE 2.2

Synthesis of 2,2-difluoro-2-(2,4-dinitro-5-fluoro-phenoxy)-N,N-diethyl-acetamide

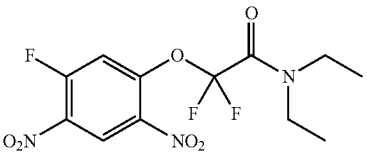 [SMILES: CCN(CC)C(=O)C(F)(F)Oc1cc(F)c([N+](=O)[O-])cc1[N+](=O)[O-]]

To a mixture of H$_2$SO$_4$ (98%, 261 g, 2.61 mol) and HNO$_3$ (100%, 107 g, 1.7 mol) at 0° C. was added 2,2-difluoro-2-(3-fluoro-phenoxy)-N,N-diethyl-acetamide (34 g, 130 mmol) with cooling. The mixture was then warmed to r.t. and stirred for further 3 h. Then, the mixture was poured on 750 g ice-water. TBME (250 mL) was added and the aqueous phase was extracted with TBME (200 mL). The combined organic phases were washed with water (300 mL), saturated NaHCO$_3$ solution and brine. Drying over Na$_2$SO$_4$ and evaporation of all volatiles gave the product as a yellow solid.

$^1$H NMR (CDCl$_3$, 500 MHz): δ (ppm)=8.82 (d, J=7.5 Hz); 7.53 (d, J=11.0 Hz, 1 H); 3.57 (q, J=7.0 Hz, 2 H); 3.45 (q, J=7.0 Hz, 2 H); 1.27 (t, J=7.0 Hz, 3 H); 1.18 (t, J=7.0 Hz, 3 H).

¹³C NMR (CDCl₃, 125 MHz): δ (ppm)=157.6 (d, J=268 Hz); 156.6 (t, J=34 Hz); 148.2 (d, J=11 Hz); 137.3; 133.3 (d, J=8 Hz); 124.7; 115.8 (t, J=281 Hz); 112.3 (d, J=26 Hz); 42.3; 42.0; 14.1; 12.2.

EXAMPLE 2.3

Synthesis of 2,2-difluoro-2-(2,4-dinitro-5-fluoro-phenoxy)-1-pyrrolidine-1-yl-ethanone

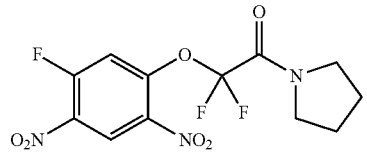 [SMILES: O=C(N1CCCC1)C(F)(F)Oc1cc(F)c([N+](=O)[O-])cc1[N+](=O)[O-]]

To a mixture of H₂SO₄ (98%, 22.0 g, 220 mmol) and HNO₃ (100%, 8.5 g, 135 mmol) at 0° C. was added 2,2-difluoro-2-(3-fluoro-phenoxy)-1-pyrrolidine-1-yl-ethanone (3.3 g, 12.7 mmol). The temperature rose to 10° C. and was kept at that temperature for further 16 h. The mixture was then poured on 150 g of ice-water and 80 mL of TBME. The aqueous phase was extracted with 50 mL of TBME. The combined org. phases were washed with saturated NaHCO₃ solution and water. The crude product (3.6 g, >98% purity by HPLC, 10.3 mmol, 81% yield) was obtained after removal of all volatiles as a yellow solid.

¹H NMR (CDCl₃, 500 MHz): δ (ppm)=8.81 (d, J=7.5 Hz, 1 H); 7.54 (d, J=11.0 Hz, 1 H); 3.72-3.78 (m, 4 H); 3.54-3.59 (m, 4 H); 2.02-2.09 (m, 4 H); 1.92-1.98 (m, 4 H).

¹³C NMR (CDCl₃, 125 MHz): δ (ppm)=157.6 (d, J=274 Hz); 155.7 (t, J=34 Hz); 148.2 (d, J=11 Hz); 137.4; 133.3 (d, J=8 Hz); 124.7; 115.6 (t, J=280 Hz); 112.5 (d, J=32 Hz); 47.9; 47.0; 26.4; 23.5.

Melting point: 78° C.

EXAMPLE 2.4

Synthesis of 2,2-difluoro-2-(2,4-dinitro-5-fluoro-phenoxy)-1-morpholine-1-yl-ethanone

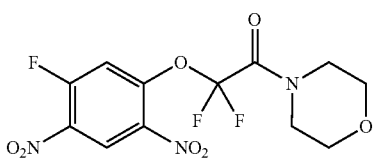 [SMILES: O=C(N1CCOCC1)C(F)(F)Oc1cc(F)c([N+](=O)[O-])cc1[N+](=O)[O-]]

To a mixture of H₂SO₄ (96%, 68.8 g, 701 mmol) and HNO₃ (100%, 13.3 g, 210 mmol) at 0° C. was added 2,2-difluoro-2-(3-fluoro-phenoxy)-1-morpholine-1-yl-ethanone (18.3 g, 90% pure, 60 mmol). The temperature was eventually increased to 40° C. and was kept at room temperature for 60 min. The mixture was then poured on 160 g of ice-water and 80 g of chlorobenzene. The aqueous phase was extracted with chlorobenzene (2×40 mL). The combined org. phases were washed with saturated NaHCO₃ solution and water. The crude product (12.3 g, >90% purity by HPLC) was obtained after removal of all volatiles as a reddish solid. Recrystallisation from n-BuOH (150 mL) gave the product as a yellow solid.

¹H NMR (CDCl₃, 500 MHz): δ (ppm)=8.82 (d, J=7.0 Hz, 1 H); 7.52 (d, J=10.5 Hz, 1 H); 3.68-3.78 (m, 8 H).

¹³C NMR (CDCl₃, 125 MHz): δ (ppm)=157.5 (d, J=274 Hz); 155.8 (t, J=34 Hz); 147.6 (d, J=11 Hz); 137.2; 135.3; 124.7; 115.4 (t, J=281 Hz); 112.1 (d, J=26 Hz); 66.5; 66.4; 46.6; 43.8.

Melting point: 96° C.

EXAMPLE 2.5

Synthesis of 2,2-difluoro-2-(5-fluoro-2-nitro-phenoxy)-N,N-dimethyl-acetamide

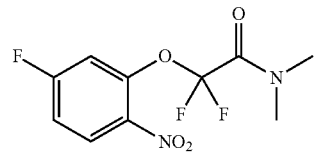 [SMILES: CN(C)C(=O)C(F)(F)Oc1cc(F)ccc1[N+](=O)[O-]]

Nitric acid (100%, 200 mL, 4.8 mol) was cooled to −5° C. 2,2-Difluoro-2-(3-fluoro-phenoxy)-N, N-L dimethyl-acetamide (19.0 g, 81.5 mmol) was added at rate to keep the temperature below −2° C. Upon complete addition stirring was continued for 30 min. The reaction mixture was then poured on 450 mg ice-water. The aqueous phase was extracted with TBME (3×100 mL); the combined organic phases were washed with water (100 mL) and brine (100 mL) and dried over MgSO₄. Evaporation of the solvent gave the crude product that was purified by preparative HPLC. The product (5.4 g, 72% by HPLC, 5% yield) was obtained as a yellow solid. Repeated chromatography gave purer material.

¹H NMR (CDCl₃, 500 MHz): δ (ppm)=8.04 (dd, J=5.5 Hz, J=9.0 Hz, 1 H); 7.26-7.29 (m, 1 H); 7.13 (dd, J=2.5 Hz, J=7.5 Hz, 1 H); 3.25 (s, 3 H); 3.09 (s, 3 H).

¹³C NMR (CDCl₃, 125 MHz): δ (ppm)=164.5 (d, J=258 Hz); 157.9 (t, J=34 Hz); 143.9 (d, J=11 Hz); 138.9; 127.9 (d, J=11 Hz); 115.5 (t, J=278 Hz); 113.6 (d, J=10 Hz); 110.9 (d, J=28 Hz); 37.2; 37.1.

EXAMPLE 2.6

Synthesis of 2,2-difluoro-2-(5-fluoro-4-nitro-phenoxy)-N,N-dimethyl-acetamide

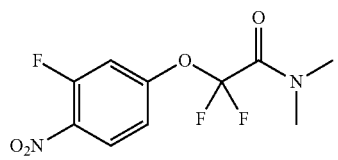 [SMILES: CN(C)C(=O)C(F)(F)Oc1ccc([N+](=O)[O-])c(F)c1]

Nitric acid (100%, 200 mL, 4.8 mol) was cooled to −5° C. 2,2-Difluoro-2-(3-fluoro-phenoxy)-N, L dimethyl-acetamide (19.0 g, 81.5 mmol) was added at rate to keep the temperature below −2° C. Upon complete addition stirring was continued for 30 min. The reaction mixture was then poured on 450 mg ice-water. The aqueous phase was extracted with TBME (3×100 mL); the combined organic phases were washed with water (100 mL) and brine (100 mL) and dried over MgSO₄. Evaporation of the solvent gave the crude product that was purified by preparative HPLC. The product (6.5 g, >98% by HPLC, 28% yield) was obtained as a yellow solid.

$^1$H NMR (DMSO-d$_6$, 500 MHz): δ (ppm)=8.31 (t, J=9.0 Hz, 1 H); 7.68 (dd, J=2.5 Hz, J=12.0 Hz, 1 H); 7.38-7.41 (m, 1 H); 3.21 (s, 3 H), 3.00 (m, 3 H).

$^{13}$C NMR (DMSO-d$_6$, 125 MHz): δ (ppm)=157.1 (t, J=34 Hz); 155.4 (d, J=262 Hz); 153.6 (d, J=11 Hz); 134.7 (d, J=7 Hz); 128.2 (d, J=2 Hz); 116.8 (d, J=4 Hz); 115.3 (t, J=274 Hz); 111.0 (d, J=25 Hz); 36.8; 36.4.

EXAMPLE 2.7

Synthesis of 2,2-difluoro-2-(5-fluoro-2-nitro-phenoxy)-N,N-dimethyl-acetamide

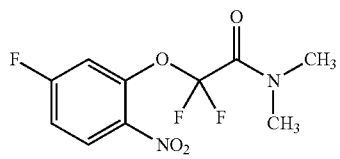 [SMILES: CN(C)C(=O)C(F)(F)Oc1cc(F)ccc1[N+](=O)[O-]]

A mixture of 2-nitro-5-fluoro-phenol (3.0 g, 19.1 mmol), 2-bromo-2,2-difluoro-N,N-dimethyl-acetamide (3.9 g, 19.1 mmol) and Na$_2$CO$_3$ (2.1 g, 19.8 mmol) in 30 mL of DMAC was heated to 100° C. overnight. The mixture was then poured on 50 mL of H$_2$O and extracted with TBME (2×50 mL). The combined organic layers were washed with 10% NaOH (50 mL) and dried over Na$_2$SO$_4$. The crude product was obtained after evaporation of all volatiles. Purification by chromatography on silica gave the product (1.8 g, 6.4 mmol, 38% yield) as a yellow oil that solidified upon standing.

$^1$H NMR (CDCl$_3$, 500 MHz): δ (ppm)=8.04 (dd, J=5.5 Hz, J=9.0 Hz, 1 H); 7.26-7.29 (m, 1 H); 7.13 (dd, J=2.5 Hz, J=7.5 Hz, 1 H); 3.25 (s, 3 H); 3.09 (s, 3 H).

$^{13}$C NMR (CDCl$_3$, 125 MHz): δ (ppm)=164.5 (d, J=258 Hz); 157.9 (t, J=34 Hz); 143.9 (d, J=11 Hz); 138.9; 127.9 (d, J=11 Hz); 115.5 (t, J=278 Hz); 113.6 (d, J=10 Hz); 110.9 (d, J=28 Hz); 37.2; 37.1.

3. Preparation of Amino Compounds of Formula (III)

EXAMPLE 3.1

Synthesis of 2,2-difluoro-2-(2,4-diamino-5-fluoro-phenoxy)-N,N-dimethyl-acetamide

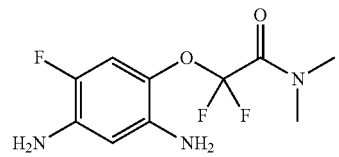

To a solution of 2,2-difluoro-2-(2,4-dinitro-5-fluoro-phenoxy)-N,N-dimethyl-acetamide (22.0 g, 68.1 mmol) in toluene (200 g) obtained according to example 2.1 alternative 2 Pd/C (10% Pd, dry catalyst, 0.7 g, 0.7 mmol) was added. Thereafter, MeOH (80 g) was added and the mixture was stirred under an atmosphere of hydrogen (pressure of 0.1 bar) at 45° C. for 90 min. After completion of the reaction the pressure was released, the catalyst was filtered off and the filtrate was evaporated to dryness. The product (17.3 g, 84% pure by NMR, 55.2 mmol, 81% yield) was obtained as an off-white solid. If desired, the purity can be increased by chromatography (SiO$_2$, cyclohexane/EtOAc mixtures).

$^1$H NMR (DMSO-d$_6$, 500 MHz): δ (ppm)=6.79 (d, J=11.0 Hz, 1 H); 6.16 (d, J=8.5 Hz, 1 H); 4.95 (bs, 2 H); 4.60 (bs, 2 H); 3.19 (s, 3 H); 2.96 (bs, 3 H).

$^{13}$C NMR (DMSO-d$_6$, 125 MHz): δ (ppm)=158.3 (t, J=35 Hz); 141.7 (d, J=278 Hz); 137.6; 134.9 (d, J=14 Hz); 123.9 (d, J=9 Hz); 115.8 (t, J=272 Hz); 109.2 (d, J=22 Hz); 102.0 (d, J=4 Hz); 36.9; 36.2.

EXAMPLE 3.2

Synthesis of 2,2-difluoro-2-(2,4-diamino-5-fluoro-phenoxy)-N,N-diethyl-acetamide

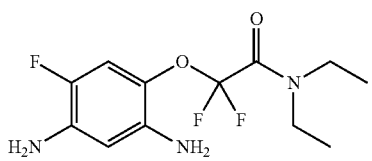

A solution of 2,2-difluoro-2-(2,4-dinitro-5-fluoro-phenoxy)-N,N-diethyl-acetamide (13.5 g, 38.4 mmol) obtained according to example 2.1 alternative 2, and Pd/C (10% Pd, dry catalyst, 2.0 g, 1.9 mmol) in MeOH (395) was stirred under an atmosphere of hydrogen (pressure of 0.1 bar) at 50° C. for 2 h. After completion of the reaction the pressure was released, the catalyst was filtered off and the filtrate was evaporated to dryness. The product was purified by column chromatography (SiO$_2$, cyclohexane/EtOAc mixtures). The product was obtained as an off-white solid (11.0 g, 88% pure by NMR, 33.2 mmol, 86% yield).

$^1$H NMR (CDCl$_3$, 500 MHz): δ (ppm)=6.85 (d, J=11.0 Hz, 1 H); 6.19 (d, J=8.5 Hz, 1 H); 3.71 (bs, 4 H); 3.58 (q, J=7.0 Hz, 2 H); 3.45 (q, J=7.0 Hz, 2 H); 1.25 (t, J=7.0 Hz, 3 H); 1.19 (t, J=7.0 Hz, 3 H).

$^{13}$C NMR (CDCl$_3$, 125 MHz): δ (ppm)=158.8 (t, J=35 Hz); 143.7 (d, J=231 Hz); 136.5; 133.5 (d, J=14 Hz); 126.9 (d, J=9 Hz); 116.1 (t, J=273 Hz); 110.3 (d, J=23 Hz); 103.8 (d, J=3 Hz); 42.4; 41.6; 14.1; 12.6.

The invention claimed is:
1. A process for manufacturing a compound of formula (I),

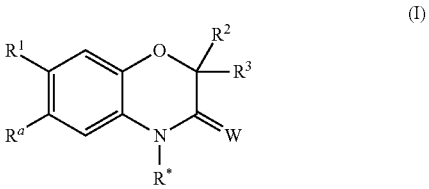

wherein
R$^1$ is H or halogen;
R$^2$ is halogen;
R$^3$ is H or halogen;
R$^a$ is H, halogen or NH$_2$;
R* is H or OH; and
W is O or S;

comprising step (i): reacting a nitro compound of formula (II),

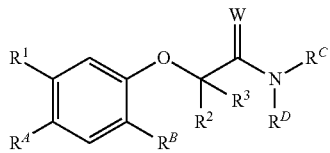
(II)

wherein $R^1$, $R^2$, $R^3$, W are defined as in formula (I);
$R^A$ is H, halogen, $NH_2$ or $NO_2$;
$R^B$ is $NO_2$; and
$R^C$, $R^D$ are independently of each other $C_1$-$C_6$-alkyl, $C_2$-$C_6$-alkenyl, $C_2$-$C_6$-alkynyl, $C_1$-$C_6$-haloalkyl, $C_1$-$C_6$-cyanoalkyl, $C_1$-$C_6$-nitroalkyl, $C_1$-$C_6$-hydroxyalkyl, $C_1$-$C_6$-alkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_3$-$C_6$-cycloalkyl, phenyl or benzyl, wherein the phenyl and the benzyl ring are independently of one another unsubstituted or substituted by 1 to 5 substituents selected from the group consisting of halogen, $NO_2$, $C_1$-$C_6$-alkyl or $C_1$-$C_6$-alkoxy, or $R^C$ and $R^D$ together with the N atom which they are attached to, represent a saturated or aromatic 3- to 6-membered ring, optionally containing 1 to 3 additional heteroatoms from the group O, S and N, with the ring optionally being substituted with 1 to 3 $C_1$-$C_6$-alkyl substituents;

with a reducing agent to obtain an amino compound of formula (III),

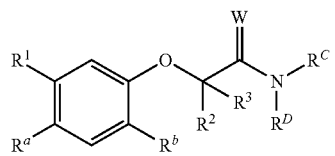
(III)

wherein $R^1$, $R^2$, $R^3$, $R^a$, W, $R^C$ and $R^D$ are defined as in formulae (I) or (II); and
$R^b$ is $NH_2$ or NHOH;

followed by step (ii): reacting the amino compound of formula (III) with an acid.

2. The process according to claim 1, wherein $R^1$ and $R^3$ are halogen.

3. The process according to claim 1, wherein
$R^A$ is $NO_2$;
$R^a$ is $NH_2$;
$R^b$ is $NH_2$; and
R* is H;
for manufacturing an NH-benzoxazinone of formula (I-1),

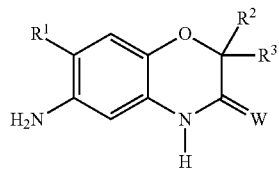
(I-1)

wherein
$R^1$ is H or halogen;
$R^2$ is halogen;
$R^3$ is H or halogen; and
W is O or S.

4. The process according to claim 1, wherein the nitro compound of formula (II) is prepared by reacting a haloacetamide of formula (IX)

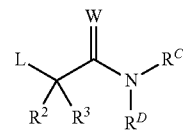
(IX)

wherein
L is halogen; and
$R^2$, $R^3$, $R^C$, $R^D$ and W are defined as in claim 1,
with a phenol compound of formula (X-1)

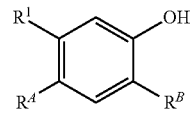
(X-1)

wherein
$R^1$, $R^A$ and $R^B$ are defined as in claim 1,
in the presence of a base.

5. The process according to claim 2, wherein
$R^A$ is $NO_2$;
$R^a$ is $NH_2$;
$R^b$ is $NH_2$; and
R* is H;
for manufacturing an NH-benzoxazinone of formula (I-1),

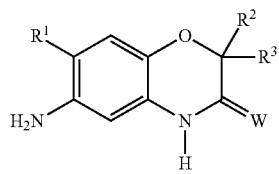
(I-1)

wherein
$R^1$ is H or halogen;
$R^2$ is halogen;
$R^3$ is H or halogen; and
W is O or S.

6. The process according to claim 2, wherein the nitro compound of formula (II) is prepared by reacting a haloacetamide of formula (IX)

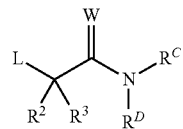
(IX)

wherein
L is halogen; and
$R^2$, $R^3$, $R^C$, $R^D$ and W are defined as in claim 1, with a phenol compound of formula (X-1)

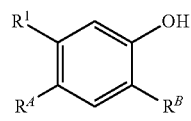
(X-1)

wherein
$R^1$, $R^A$ and $R^B$ are defined as in claim 1,
in the presence of a base.

7. The process according to claim 3, wherein the nitro compound of formula (II) is prepared by reacting a haloacetamide of formula (IX)

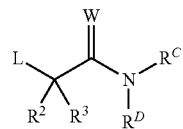
(IX)

wherein
L is halogen; and
$R^2$, $R^3$, $R^C$, $R^D$ and W are defined as in claim 1,
with a phenol compound of formula (X-1)

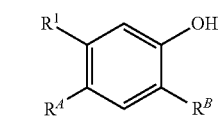
(X-1)

wherein
$R^1$, $R^A$ and $R^B$ are defined as in claim 1,
in the presence of a base.

8. A benzoxazinone of formula (Ia.1.1), (Ia.1.1)

wherein
R* is H or OH.

9. A benzoxazinone of formula (Ia.1.1) according to claim 8, wherein R* is H.

10. The process of claim 1, wherein step (i) is carried out at a pH below 7.

* * * * *